United States Patent [19]
Helal

[11] Patent Number: 4,634,445
[45] Date of Patent: Jan. 6, 1987

[54] JOINT PROSTHESIS

[75] Inventor: Basil H. Helal, Cheshunt, United Kingdom

[73] Assignee: OEC Europe Limited, United Kingdom

[21] Appl. No.: 344,169

[22] Filed: Jan. 29, 1982

[30] Foreign Application Priority Data

Jan. 30, 1981 [GB] United Kingdom ............... 8102977

[51] Int. Cl.[4] ............................................. A61F 2/42
[52] U.S. Cl. ................................................... 623/21
[58] Field of Search ................ 3/1.9, 1.91; 128/92 C

[56] References Cited

U.S. PATENT DOCUMENTS

| | | | |
|---|---|---|---|
| 3,462,765 | 8/1969 | Swanson | 3/1.91 |
| 3,739,403 | 6/1973 | Nicole | 3/1.91 |
| 3,818,513 | 6/1974 | Pillet | 128/92 C X |
| 4,158,893 | 6/1979 | Swanson | 3/1.91 |
| 4,204,284 | 5/1980 | Koeneman | 3/1.91 |
| 4,246,662 | 1/1981 | Pastrick | 3/1.91 |
| 4,313,232 | 2/1982 | Habal et al. | 3/1.91 |
| 4,367,562 | 1/1983 | Gauthier | 3/1.91 |

*Primary Examiner*—Richard J. Apley
*Assistant Examiner*—David J. Isabella
*Attorney, Agent, or Firm*—Hall, Myers & Rose

[57] ABSTRACT

A small joint spacing prosthesis comprises an elongate silicone rubber body reinforced by a Dacron or nylon string and is made by moulding the body with the string therein. The middle of the body forms a spacer of spherical shape with flat end faces providing shoulders for abutment of the bone ends. The remainder of the body forms intramedullary stems with rounded outer ends.

11 Claims, 1 Drawing Figure

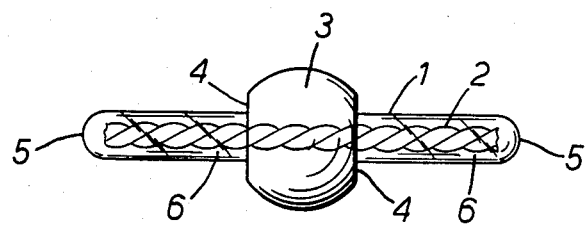

JOINT PROSTHESIS

BACKGROUND OF THE INVENTION

Field of the Invention

This invention relates to a joint prosthesis, particularly a small joint spacing prosthesis usable in the hands and feet.

SUMMARY OF THE INVENTION

According to the present invention, there is provided a joint prosthesis, comprising a spacer for insertion between first and second bones, and first and second intramedullary stems extending from respective opposite ends of said spacer for insertion into the respective bones, the spacer being of greater width than the stems, thereby providing shoulders against which the respective ends of the bones can abut, the arrangement being such that, in the prosthesis when implanted, bending of the joint occurs at the respective end zones of the stems nearer the spacer.

BRIEF DESCRIPTION OF THE DRAWINGS

In order that the invention may be clearly understood and readily carried into effect, reference will now be made, by way of example, to the accompanying drawing, which shows an elevation of a joint prosthesis.

DESCRIPTION OF THE PREFERRED EMBODIMENT

Referring to the drawing, the prosthesis is a small joint spacing prosthesis which is usable in the hands and feet and would in practice be provided in various sizes. It consists of an elongate silicone rubber body 1 reinforced by a Dacron or nylon string 2, and has been made by moulding the body 1 with the string 2 therein. The middle of the body 1 is of increased diameter to form a spacer 3 which is of spherical shape except that it has flat end faces 4. The remaining parts of the body 1 are of constant diameter except at their rounded ends 5 and form intramedullary stems 6 projecting centrally from the respective end faces 4.

During implantation the stems 6 are inserted into resectioned adjacent ends of respective bones and the spacer 3 positioned between the resectioned ends abutting against the end faces 4.

The prosthesis can be used in replacements of metacarpo-phalangeal joints, metatarso-phalangeal joints, proximal interphalangeal joints of the fingers, and the carpo-metacarpal joint of the thumb, for example. From a cosmetic viewpoint, in a metacarpo-phalangeal joint, the prosthesis reproduces the knuckle feature. Bending of the joint occurs at the two inner end zones of the stem 6. Because the bone ends abut the definite limits provided by the faces 4, there is no tendency for the stems 6 to penetrate more deeply into the medullae during use of the joint.

I claim:

1. A joint prosthesis comprising:
   a spacer for insertion between first and second bones, and,
   first and second intermedullary stems extending from opposite ends of said spacer for insertion into said bones and remaining slidable within said bones,
   the spacer having a greater width than the stems and thus is relatively more rigid than said stems,
   said spacer including at least two shoulders,
   said shoulders being designed and arranged to abut said bones when said stems are implanted therein
   where the spacer is spherically shaped and said shoulders define flat end faces,
   said spacer and said stems being designed and arranged such that when the prosthesis is implanted in said bones, bending of the joint prosthesis occurs in each of the stems and not in the spacer.

2. A prosthesis according to claim 1, wherein said one piece has been molded with said flexible member therein.

3. A prosthesis according to claim 1, wherein said stems have their terminal ends rounded.

4. A joint prosthesis according to claim 1 wherein said prosthesis is comprised of an elastomeric material.

5. A joint prosthesis according to claim 4 wherein said prosthesis has an elongated flexible member embedded therein.

6. A joint prosthesis according to claim 5 wherein said flexible member is a piece of string.

7. A joint prosthesis according to claim 1 wherein said spacer and said stems are in one piece and are made of unitary elastomeric material.

8. A joint prosthesis according to claim 7 wherein said spacer and said stems have an elongated flexible member embedded therein.

9. A joint prosthesis according to claim 8 wherein said flexible member is a piece of string.

10. A joint prosthesis according to claim 1 wherein said spacer and said stems are a solid piece of elastomeric material having a flexible member embedded therein.

11. A joint prosthesis according to claim 10 where said stems are of a substantially constant thickness.